United States Patent
Lee et al.

(10) Patent No.: US 12,187,671 B2
(45) Date of Patent: Jan. 7, 2025

(54) METHODS OF ETHERIFICATION

(71) Applicant: Dow Global Technologies LLC, Midland, MI (US)

(72) Inventors: Wen-Sheng Lee, Midland, MI (US); Sung-Yu Ku, Freeport, TX (US); Stephen W. King, League City, TX (US)

(73) Assignee: Dow Global Technologies LLC, Midland, MI (US)

( * ) Notice: Subject to any disclaimer, the term of this patent is extended or adjusted under 35 U.S.C. 154(b) by 414 days.

(21) Appl. No.: 17/637,610

(22) PCT Filed: Sep. 23, 2020

(86) PCT No.: PCT/US2020/052139
§ 371 (c)(1),
(2) Date: Feb. 23, 2022

(87) PCT Pub. No.: WO2021/067087
PCT Pub. Date: Apr. 8, 2021

(65) Prior Publication Data
US 2022/0281792 A1    Sep. 8, 2022

Related U.S. Application Data

(60) Provisional application No. 62/907,911, filed on Sep. 30, 2019.

(51) Int. Cl.
| | |
|---|---|
| *C07C 41/06* | (2006.01) |
| *B01J 29/70* | (2006.01) |
| *B01J 37/08* | (2006.01) |
| *C07C 41/09* | (2006.01) |

(52) U.S. Cl.
CPC .......... *C07C 41/06* (2013.01); *B01J 29/7007* (2013.01); *B01J 37/08* (2013.01); *C07C 41/09* (2013.01); *B01J 2229/16* (2013.01); *B01J 2229/32* (2013.01)

(58) Field of Classification Search
CPC ................ C07C 41/05; C07C 41/06
See application file for complete search history.

(56) References Cited

U.S. PATENT DOCUMENTS

| | | | | |
|---|---|---|---|---|
| 4,906,787 | A * | 3/1990 | Huang .................... | C07C 41/06 568/897 |
| 5,144,084 | A | 9/1992 | Marler et al. | |
| 7,807,615 | B2 | 10/2010 | Stephan et al. | |
| 8,766,015 | B2 * | 7/2014 | Kim ........................ | C07C 41/44 568/619 |
| 2001/0007047 | A1 | 7/2001 | Onda et al. | |
| 2009/0240086 | A1 | 9/2009 | Barsa et al. | |

FOREIGN PATENT DOCUMENTS

| | | | | |
|---|---|---|---|---|
| EP | 0419077 | A2 * | 3/1991 | ............. C07C 41/06 |
| JP | 2000300994 | A | 10/2000 | |
| WO | WO1990008120 | A1 * | 7/1990 | ............. C07C 29/04 |
| WO | 2013146370 | A1 | 10/2013 | |

OTHER PUBLICATIONS

International Preliminary Report on Patentability for related PCT Application PCT/US2020/052139, mailed Apr. 14, 2022 (7 pgs).
International Search Report & Written Opinion for related PCT Application PCT/US2020/052139, mailed Dec. 17, 2020 (12 pgs).
Wang et al., "Effects of H β Modification on Acidity and Activity for Propene Hydration Etherification", Journal of Fuel Chemistry and Technology, vol. 30, No. 4, pp. 353-357, Aug. 2002.

* cited by examiner

*Primary Examiner* — Medhanit W Bahta
(74) *Attorney, Agent, or Firm* — Arthur R. Rogers

(57) ABSTRACT

Embodiments of the present disclosure are directed towards methods of etherification including modifying a zeolite catalyst with silica to provide a silica modified zeolite catalyst; and contacting the silica modified zeolite catalyst with an olefin and an alcohol to produce a monoalkyl ether.

8 Claims, No Drawings

METHODS OF ETHERIFICATION

This application is a National Stage Application under 35 U.S.C. § 371 of International Application Number PCT/US2020/052139, filed Sep. 23, 2020, and published as WO 2021/067087 on Apr. 8, 2021, which claims the benefit to U.S. Provisional Application 62/907,911, filed Sep. 30, 2019, the entire contents of which are incorporated herein by reference in its entirety.

FIELD OF DISCLOSURE

Embodiments of the present disclosure are directed towards methods of etherification more specifically, embodiments are directed towards methods of etherification including modifying a zeolite catalyst with silica to provide a silica modified zeolite catalyst and producing a monoalkyl ether by contacting the silica modified zeolite catalyst with an olefin and an alcohol.

BACKGROUND

Monoalkyl ethers are useful for a number of applications such as solvents, surfactants, and chemical intermediates, for instance. There is continued focus in the industry on developing new and improved materials and/or methods that may be utilized for making monoalkyl ethers.

SUMMARY

The present disclosure provides methods of etherification, the methods including modifying a zeolite catalyst with silica to provide a silica modified zeolite catalyst having a silica loading from 15 to 50 weight percent based upon a total weight of the silica modified zeolite catalyst; and producing a monoalkyl ether by contacting the silica modified zeolite catalyst with an olefin and an alcohol.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Methods of etherification are disclosed herein. The methods include modifying a zeolite catalyst with silica to provide a silica modified zeolite catalyst and producing a monoalkyl ether by contacting the silica modified zeolite catalyst with an olefin and an alcohol.

Advantageously, the methods of etherification disclosed herein can provide an improved, i.e. greater, monoalkyl ether selectivity, as compared to etherifications that do not utilize the silica modified zeolite catalyst, as discussed further herein. Improved monoalkyl ether selectivity, can be desirable for a number of applications, such as providing chemical intermediates. As an example, the monoalkyl ether may be utilized in a surfactant production by ethoxylation process, where the monoalkyl ether can desirably influence the surfactant's properties, e.g. as compared to a dialkyl ether that can undesirably influence the surfactant's properties.

Additionally, the methods of etherification disclosed herein can provide an improved, i.e. lesser, dialkyl ether selectivity, as compared to etherifications that do not utilize the silica modified zeolite catalyst, as discussed further herein. Improved dialkyl ether selectivity can be desirable for a number of applications, such as a surfactant production by ethoxylation process, where the dialkyl ether can undesirably influence the surfactant's properties, e.g. as compared to a monoalkyl ether.

Zeolite catalysts are crystalline metallosilicates, e.g., aluminosilicates, constructed of repeating $TO_4$ tetrahedral units where T may be Si, Al or P (or combinations of tetrahedral units), for example. These units are linked together to form frameworks having regular intra-crystalline cavities and/or channels of molecular dimensions, e.g., micropores.

Embodiments of the present disclosure provide that the zeolite catalyst is a synthetic zeolite catalyst. Synthetic zeolite catalysts can be made by a known process of crystallization of a silica-alumina gel in the presence of alkalis and templates, for instance. Examples include zeolite beta catalysts (BEA), Linde Type A (LTA), Linde Types X and Y (Al-rich and Si-rich FAU), Silicalite-1, ZSM-5 (MFI), Linde Type B (zeolite P), Linde Type F (EDI), Linde Type L (LTL), Linde Type W (MER), and SSZ-32 (MTT) as described using IUPAC codes in accordance with nomenclature by the Structure Commission of the International Zeolite Association. IUPAC codes describing Crystal structures as delineated by the Structure Commission of the International Zeolite Association refer to the most recent designation as of the priority date of this document unless otherwise indicated.

One or more embodiments provide that the zeolite catalyst a zeolite beta (BEA) catalyst. One or more embodiments provide that the zeolite catalyst includes a number of Bronsted acid sites, i.e., sites that donate protons.

The zeolite catalyst can have a $SiO_2/Al_2O_3$ mole ratio from 5:1 to 1500:1 as measured using Neutron Activation Analysis. All individual values and subranges from 5:1 to 1500:1 are included; for example, the zeolite catalyst can have a $SiO_2/Al_2O_3$ mole ratio from a lower limit of 5:1, 10:1, 15:1, or 20:1 to an upper limit of 1500:1, 750:1, 300:1, or 100:1.

The zeolite catalyst can have a mean pore diameter from 5 to 12 angstroms. All individual values and subranges from 5 to 12 angstroms are included; for example, the zeolite catalyst can have a mean pore diameter from a lower limit of 5 or 7 angstroms to an upper limit of 11 or 12 angstroms.

The zeolite catalyst can have surface area from 130 to 1000 $m^2/g$. All individual values and subranges from 130 to 1000 $m^2/g$ are included; for example, the zeolite catalyst can have a surface area from a lower limit of 130, 150, 175, 300, 400, or 500 $m^2/g$ to an upper limit of 1000, 900, or 800 $m^2/g$. Surface area is measured according to ASTM D4365-19.

As mentioned, the zeolite catalyst can be made by a process that utilizes a template, which may also be referred to as an organic template. Templates may also be referred to as templating agents and/or structure-directing agents (SDAs). The template can be added to the reaction mixture for making the zeolite catalyst to guide, e.g., direct, the molecular shape and/or pattern of the zeolite catalyst's framework. When the zeolite catalyst making process is completed, the zeolite catalyst includes templates, e.g., templates located in the micropores of the zeolite catalyst. Templates are utilized in the formation of the zeolite catalyst. One or more embodiments provides that the template comprises ammonium ions. Zeolite catalyst that include templates can be made by known processes. Zeolite catalyst that include templates can be obtained commercially. Examples of suitable commercially available metallosilicate catalysts include CP814E, CP814C, CP811C-300, CBV 712, CBV 720, CBV 760, CBV 2314, CBV 10A from ZEOLYST INTERNATIONAL™ of Conshohocken, PA.

Various templates that may be utilized for making zeolite catalysts are known. Examples of templates include tetraethylammonium hydroxide; N,N,N-trimethyl-1-adamanteammonium hydroxide; hexamethyleneimine; and dibenzylmethylammonium; among others.

Embodiments of the present disclosure provide modifying a zeolite catalyst with silica to provide a silica modified zeolite catalyst. Modifying the zeolite catalyst maybe performed via a number of known processes, such as an impregnation process or a solution process, for instance, followed by calcination. Modifying the zeolite catalyst with silica may utilize known conditions and may utilize know equipment and known components. For instance, the zeolite catalyst may be contacted with an aqueous solution and/or an organic solvent including a silicon compound. Examples of the organic solvent include, but are not limited to, hexane, toluene, and combinations thereof. Examples of the silicon compound include, but are not limited to, tetramethyl orthosilicate, tetraethyl orthosilicate, and combinations thereof. Modifying the zeolite catalyst provides that the zeolite catalyst is loaded with silica from the silicon compound.

Modifying a zeolite catalyst with silica can include contacting the zeolite catalyst with a solution including a silicon compound, followed by calcination. The solution may include water and/or an organic solvent. Various amounts of silicon compound and/or water and/or organic solvent may be utilized for different applications.

The zeolite catalyst may be contacted with the solution including the silica compound at temperature from 5° C. to 90° C., for example. All individual values and subranges from 5° C. to 90° C. are included; for example, the zeolite catalyst may be contacted with the solution including the silica compound at temperature from a lower limit of 5, 10, or 15° C. to an upper limit of 90, 85, or 80° C.

The zeolite catalyst may be contacted with the solution including the silica compound for 0.5 hours to 96 hours, for example. All individual values and subranges from 0.5 hours to 96 hours are included; for example, the zeolite catalyst may be contacted with the solution including the silica compound from a lower limit of 0.5, 0.8, or 1 hours to an upper limit of 96, 72, 48, 24, or 12 hours.

One or more embodiments of the present disclosure provide that a number of steps of modifying the zeolite catalyst, as discussed may be repeated. For example, the zeolite catalyst may be contacted with the solution including the silica compound multiple times. When steps of modifying the zeolite catalyst are repeated, a subsequent step may utilize the same conditions and/or components of a previous step. When steps of modifying the zeolite catalyst are repeated, a subsequent step may utilize different conditions and/or components of a previous step.

The silica modified zeolite catalyst has a silica loading from 15 to 50 weight percent based upon a total weight of the silica modified zeolite catalyst. In other words, modifying the zeolite catalyst with the silicon compound, followed by calcination adds silica to the silica modified zeolite catalyst. All individual values and subranges from 15 to 50 weight percent are included; for example, the silica modified zeolite catalyst can have a silica loading from a lower limit of 15, 20, 20.5, 21, or 21.5 weight percent to an upper limit of 50, 45, 40, 39, or 38 weight percent based upon a total weight of the silica modified zeolite catalyst. Silica loading is determined by a known process. Silica loading is calculated based upon components utilized to make the silica modified zeolite catalyst. For instance, silicon and aluminum loading of the silica modified zeolite beta catalyst are determined by elemental analysis (neutron activation analysis); a known amount of aluminum of the zeolite catalyst, e.g., based upon a structure of the zeolite catalyst, is utilized to then calculate the silica loading of the silica modified zeolite catalyst.

One or more embodiments of the present disclosure provide that following contacting zeolite catalyst with the silicon compound, the zeolite catalyst can be calcined to provide the silica modified zeolite catalyst. The zeolite catalyst can be calcined at a temperature from 350° C. to 700° C. to provide the silica modified zeolite catalyst. All individual values and subranges from 350° C. to 700° C. are included; for example, the zeolite catalyst may be calcined at from a lower limit of 350° C., 400° C., or 450° C. to an upper limit of 700° C., 650° C., or 600° C.

The zeolite catalyst can be calcined in a number of known calcination environments. For instance, the zeolite catalyst may be calcined in an air environment.

The zeolite catalyst may be calcined, i.e., exposed to a temperature from 350° C. to 700° C. in a calcination environment, from 1 hour to 24 hours. All individual values and subranges from 1 hour to 24 hours are included; for example, the zeolite catalyst may be calcined at from a lower limit of 1 hour, 3 hours, or 6 hours to an upper limit of 24 hours, 18 hours, or 12 hours.

One or more embodiments provide that the methods disclosed herein include reducing, e.g., removing, templates of the zeolite catalyst prior to modifying the zeolite catalyst with silica, as discussed herein. Embodiments of the present disclosure provide that templates of the zeolite catalyst can be reduced by calcination.

To reduce templates, the zeolite catalyst may be calcined at temperature from 550° C. to 750° C. All individual values and subranges from 550° C. to 750° C. are included; for example, the zeolite catalyst may be calcined at from a lower limit of 550° C., 560° C., or 575° C. to an upper limit of 750° C., 700° C., or 650° C. to reduce templates.

To reduce templates, the zeolite catalyst may be calcined in a number of known calcination environments. For instance, the zeolite catalyst may be calcined in an air environment.

To reduce templates, the zeolite catalyst may be calcined, i.e., exposed to a temperature from 550° C. to 750° C. in a calcination environment, from 1 hour to 24 hours. All individual values and subranges from 1 hour to 24 hours are included; for example, the zeolite catalyst may be calcined at from a lower limit of 1 hour, 3 hours, or 6 hours to an upper limit of 24 hours, 18 hours, or 12 hours.

Embodiments of the present disclosure are directed towards methods of etherification. Etherification refers to a chemical process, e.g., chemical reaction, that produces ethers. The methods disclosed herein include producing a monoalkyl ether by contacting the silica modified zeolite catalyst with an olefin and an alcohol.

As used herein, "olefin" refers to a compound that is a hydrocarbon having one or more carbon-carbon double bonds. Embodiments of the present disclosure provide that the olefin includes from 6 to 30 carbon atoms. All individual values and subranges from 6 to 30 carbon atoms are included; for example, the olefin can include a lower limit of 6, 8, or 10 carbons to an upper limit of 30, 20, or 14 carbons.

The olefin may include alkenes such as alpha ($\alpha$) olefins, internal disubstituted olefins, or cyclic structures (e.g., $C_3$-$C_{12}$ cycloalkene). Alpha olefins include an unsaturated bond in the α-position of the olefin. Suitable α olefins may be selected from the group consisting of propylene, 1-butene, 1-hexene, 4-methyl-1-pentene, 1-heptene, 1-octene, 1-decene, 1-dodecene, 1-tetradecene, 1-hexadecene, 1-octadecene, 1-icosene, 1-docosene and combinations thereof. Internal disubstituted olefins include an unsaturated bond not in a terminal location on the olefin. Internal olefins may be selected from the group consisting of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene and combinations thereof. Other exemplary olefins may include butadiene and styrene.

Examples of suitable commercially available olefins include NEODENE™ 6-XHP, NEODENE™ 8, NEODENE™ 10, NEODENE™ 12, NEODENE™ 14, NEODENE™ 16, NEODENE™ 1214, NEODENE™ 1416, NEODENE™ 16148 from Shell, The Hague, Netherlands.

Embodiments of the present disclosure provide that the alcohol may comprise a single hydroxyl group, may comprise two hydroxyl groups, i.e., a glycol, or may comprise three hydroxyl groups. The alcohol may include 1 carbon or greater, or 2 carbons or greater, or 3 carbons or greater, or 4 carbons or greater, or 5 carbons or greater, or 6 carbons or greater, or 7 carbons or greater, or 8 carbons or greater, or 9 carbons or greater, while at the same time, 10 carbons or less, or 9 carbons or less, or 8 carbons or less, or 7 carbons or less, or 6 carbons or less, or 5 carbons or less, or 4 carbons or less, or 3 carbons or less, or 2 carbons or less. The alcohol may be selected from the group consisting of methanol, ethanol, monoethylene glycol, diethylene glycol, propylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, 1,4-cyclohexanemethanediol, glycerol and, combinations thereof. One or more embodiments provide that the alcohol is selected from the group consisting of monoethylene glycol, diethylene glycol, glycerol, and combinations thereof. One or more embodiments provide that the alcohol is a (poly)alkylene glycol such as monoethylene glycol, diethylene glycol, propylene glycol, or triethylene glycol. Examples of (poly)alkylene glycols include monoethylene glycol, diethylene glycol, triethylene glycol, polyethylene glycol, monopropylene glycol, dipropylene glycol, tripropylene glycol, polypropylene glycol, 1,3-propane diol, 1,2-butane diol, 2,3-butane diol, 1,4-butane diol, 1,6-hexane diol, paraxylene glycol, glycerol, and 1,4-cyclohexane methane diol. One or more embodiments provide that the (poly)alkylene glycol is monoethylene glycol.

Embodiments of the present disclosure provide that the alcohol and the olefin are reacted, e.g. contacted with the silica modified zeolite catalyst, at a molar ratio of 0.05:1 to 20:1 moles of alcohol to moles of olefin. All individual values and subranges from 0.05:1 to 20:1 are included; for example, the alcohol and the olefin can be reacted at lower limit of 0.05:1, 0.075:1, or 0.1:1 to an upper limit of 20:1, 18:1, or 15:1 moles of alcohol to moles of olefin.

As mentioned, methods disclosed herein include contacting the silica modified zeolite catalyst with an olefin and an alcohol to produce a monoalkyl ether. The olefin and the alcohol may contact the silica modified zeolite catalyst under known etherification conditions and may utilize know reaction equipment and known reaction components. For instance, the olefin and the alcohol may contact the reduced template zeolite catalyst in a slurry reactor, a fixed-bed reactor, or a fluidized-bed reactor. The reactor may operate in batch mode or continuous mode.

The silica modified zeolite catalyst may be utilized in an amount such that the silica modified zeolite catalyst is from 1% to 50% by weight based upon a total weight of the olefin, for instance. All individual values and subranges from 1% to 50% by weight are included; for example, the silica modified zeolite catalyst can be from a lower limit of 1%, 3%, or 5% to an upper limit of 50%, 40%, or 30% by weight based upon a total weight of the olefin.

The olefin and the alcohol may contact the silica modified zeolite catalyst at a reaction temperature from 80° C. to 200° C. All individual values and subranges from 80° C. to 200° C. are included; for example, the olefin and the alcohol may contact the silica modified zeolite catalyst from a lower limit of 80, 90, or 100° C. to an upper limit of 200, 175, or 150° C.

The reaction pressure may vary for different applications. For instance, the reaction pressure may be a reduced pressure, an atmospheric pressure, or an increased pressure.

Contacting the silica modified zeolite catalyst with the olefin and the alcohol produces a monoalkyl ether. Various monoalkyl ethers may be produced for different applications, e.g., by varying which olefin is utilized and/or by varying which alcohol is utilized. Advantageously, the methods of etherification disclosed herein can provide an improved, i.e. greater, monoalkyl ether selectivity, as compared to etherifications that do not utilize the silica modified zeolite catalyst as described herein.

Additionally, the methods of etherification disclosed herein can provide an improved, i.e. lesser, dialkyl ether selectivity, as compared to etherifications that do not utilize the silica modified zeolite catalyst as described herein.

Examples

In the Examples, various terms and designations for materials are used including, for instance, the following:

Zeolite beta catalyst (CP 814E, CAS No. 1318-02-1 $SiO_2/Al_2O_3$ mole ratio of 25:1; mean pore diameter 6.7 angstroms; surface area 680 m²/g; all organic templates were removed by commercial supplier prior to receipt; obtained from Zeolyst International);

Zeolite beta catalyst (CP 806EL, CAS No. 1318-02-1 $SiO_2/Al_2O_3$ mole ratio of 25:1; mean pore diameter angstroms; surface area 177 m²/g; including organic templates as obtained; obtained from Zeolyst International).

Example 1 was performed as follows. Zeolite beta catalyst was modified with silica as follows. Zeolite beta catalyst (CP 806EL, 60 grams) was added to hexane (800 mL) in a container (1 L). Tetraethyl orthosilicate (40 mL) was added to the contents of the container while stirring; then contents of the container were stirred at ambient conditions for 96 hours. Then, solvent was removed by rotary evaporation and the dried zeolite beta catalyst was calcined at 550° C. in an air environment for 8 hours. Then, the resulting material was added to hexane (800 mL) in a container (1 L). Tetraethyl orthosilicate (40 mL) was added to the contents of the container while stirring; then contents of the container were stirred at ambient conditions for 24 hours. Then, solvent was removed by rotary evaporation and the dried zeolite beta catalyst was calcined at 550° C. in an air environment for 8 hours to provide a silica modified zeolite beta catalyst. Silicon and aluminum loading of the silica modified zeolite beta catalyst was determined by elemental analysis (neutron activation analysis); the silica modified zeolite beta catalyst had additional silica loading of 37.5% based upon the total weight of the silica modified zeolite beta catalyst.

Etherification was performed as follows. The silica modified zeolite beta catalyst (0.75 grams) was added to a vial reactor (40 mL) with rare earth magnetic stir bars (Part #: VP 772FN-13-13-150, V&P Scientific, Inc.); 1-dodecene (6.2 grams) and monoethylene glycol (6.7 grams) were added to the vial reactor; the contents of the vial reactor were heated to 150° C. and stirred for 3 hours for the etherification. Then the contents of the vial reactor were analyzed by gas chromatography. The gas chromatography samples were prepared by adding contents of the vial reactor (100 μL) to 10 mL of internal standard solution (1 mL of hexadecane dissolved in 1 L of ethyl acetate) and were then analyzed offline with an Agilent GC (7890). For the analysis, dioxane, 1-dodecene (1-$C_{12}$) and isomers thereof ($C_{12}$), 2-dodecanol, diethylene glycol, monoalkyl ether and isomers thereof, and dialkyl ether and isomers thereof were included for product quantification such that the weight percent of species of interests were obtained.

Dodecene derived species were dodecyl-monoether (ME), dodecyl-diether (DE), and 2-dodcanol.

Total amount of dodecene included 1-dodecene and all non 1-dodecene other $C_{12}$ isomers.

Total amount of dodecene derived species=monoether moles+2×diether moles+2-dodecanol.

Dodecyl-monoether (ME) selectivity (%) was determined as: [total amount of ME]/[total amount of $C_{12}$ derived species]×100%.

Dodecyl-diether (DE) selectivity (%) was determined as: 2×[total amount of DE]/[total amount of $C_{12}$ derived species]×100%.

Olefin conversion (%) was determined as: [total amount of $C_{12}$ derived species]/[total amount of $C_{12}$ derived species+total amount of dodecene]×100%.

The results are reported in Table 1.

Comparative Example A was performed as Example 1 with the change that the zeolite beta catalyst (CP 806EL) was not modified with silica; 0.35 grams of catalyst was utilized rather than 0.75 grams; and the etherification reaction was 1.5 hours rather than 3 hours. The catalyst loading and/or the etherification reaction time were adjusted so that Example 1 and Comparative Example A had similar olefin conversion percents. The results are reported in Table 1.

TABLE 1

|  | Example 1 | Comparative Example A |
|---|---|---|
| Silica loading (wt %) | 37.5 | — |
| Olefin conversion (%) | 26.4 | 27.0 |
| Monoalkyl ether selectivity (%) | 95.4 | 89.0 |
| Dialkyl ether selectivity (%) | 4.6 | 11.0 |

The data of Table 1 illustrate that Example 1 had an improved, i.e. greater, monoalkyl ether selectivity as compared to Comparative Example A.

The data of Table 1 illustrate that Example 1 had an improved, i.e. lesser, dialkyl ether selectivity as compared to Comparative Example A.

Example 2 was performed as follows. Zeolite beta catalyst (CP 814E) was calcined at 550° C. in an air environment for 12 hours to convert the catalyst from $NH_4$ form to H form; then the catalyst was modified with silica as follows. Zeolite beta catalyst (41 grams) was impregnated with a solution containing hexane (80 mL) and tetraethyl orthosilicate (20 mL); the components were stirred for 5 minutes at 20° C. Then the catalyst was dried in a box oven at 200° C. for 1 hour. Then the catalyst was calcined at 550° C. in an air environment for 4 hours to provide a silica modified zeolite beta catalyst.

Etherification was performed as follows. The silica modified zeolite beta catalyst (0.75 grams) was added to a vial reactor (40 mL) with rare earth magnetic stir bars (Part #: VP 772FN-13-13-150, V&P Scientific, Inc.); 1-dodecene (6.2 grams) and monoethylene glycol (6.7 grams) were added to the vial reactor; the contents of the vial reactor were heated to 150° C. and stirred for 3 hours for the etherification. The results are reported in Table 2.

Comparative Example B was performed as Example 2 with the change that the zeolite beta catalyst (CP 814E) was not modified with silica. The results are reported in Table 2.

TABLE 2

|  | Example 2 | Comparative Example B |
|---|---|---|
| Silica loading (wt %) | 21.8 | — |
| Olefin conversion (%) | 35.2 | 37.9 |
| Monoalkyl ether selectivity (%) | 87.2 | 70.1 |
| Dialkyl ether selectivity (%) | 11.8 | 29.1 |

The data of Table 2 illustrate that Example 2 had an improved, i.e. greater, monoalkyl ether selectivity as compared to Comparative Example B.

The data of Table 2 illustrate that Example 1 had an improved, i.e. lesser, dialkyl ether selectivity as compared to Comparative Example B.

Example 3 was performed as follows. Zeolite beta catalyst (CP 814E) was calcined at 550° C. in an air environment for 12 hours to convert the catalyst from $NH_4$ form to H form; then the catalyst was modified with silica as follows. The zeolite beta catalyst (10 grams) and hexane (100 mL) were added to a container; then tetraethyl orthosilicate (16.5 grams) was added to the container and the contents of the container were stirred for 60 hours at 20° C. Then, the contents of the container were centrifuged to obtain a solid that was calcined at 550° C. in an air environment for 8 hours to provide a silica modified zeolite beta catalyst.

Etherification was performed as follows. The silica modified zeolite beta catalyst (0.75 grams) was added to a vial reactor (40 mL) with rare earth magnetic stir bars (Part #: VP 772FN-13-13-150, V&P Scientific, Inc.); 1-dodecene (6.2 grams) and monoethylene glycol (6.7 grams) were added to the vial reactor; the contents of the vial reactor were heated to 150° C. and stirred for 1 hour for the etherification. The results are reported in Table 3.

Comparative Example C was performed as Example 3 with the change that the zeolite beta catalyst (CP 814E) was not modified with silica; and 0.35 grams of catalyst was utilized rather than 0.75 grams and the etherification reaction was 1 hour. The catalyst loading was adjusted so that Example 3 and Comparative Example C had similar olefin conversion (%). The results are reported in Table 3.

TABLE 3

|  | Example 3 | Comparative Example C |
|---|---|---|
| Silica loading (wt %) | 28.4 | — |
| Olefin conversion (%) | 19.2 | 19.0 |
| Monoalkyl ether selectivity (%) | 94.0 | 91.0 |
| Dialkyl ether selectivity (%) | 4.0 | 9.0 |

The data of Table 3 illustrate that Example 3 had an improved, i.e. greater, monoalkyl ether selectivity as compared to Comparative Example C.

The data of Table 3 illustrate that Example 3 had an improved, i.e. lesser, dialkyl ether selectivity as compared to Comparative Example C.

What is claimed is:

1. A method of etherification, the method comprising:
producing a monoalkyl ether by contacting a silica modified zeolite catalyst with an olefin and an alcohol having two or more hydroxyl groups,
wherein the silica modified zeolite catalyst is modified by impregnation of a zeolite catalyst with a solution comprising a silicon compound to a silica loading from 15 to 50 weight percent based upon a total weight of the zeolite catalyst.

2. The method of claim 1, wherein the zeolite catalyst is a zeolite beta catalyst.

3. The method of claim 1, wherein the templates of the zeolite catalyst are removed prior to modification.

4. The method of claim 3, wherein removal of the reducing templates comprises calcination of the of the zeolite catalyst.

5. The method of claim 1, wherein the olefin includes from 6 to 30 carbon atoms.

6. The method claim 1, wherein the olefin is a $C_{12}$-$C_{14}$ olefin.

7. The method of claim 1, wherein the alcohol is selected from the group consisting of monoethylene glycol, diethylene glycol, glycerol, and combinations thereof.

8. The method of claim 1, wherein the silicon compound is tetramethyl orthosilicate or tetraethyl orthosilicate.

* * * * *